US007340063B1

(12) United States Patent
Nielsen et al.

(10) Patent No.: US 7,340,063 B1
(45) Date of Patent: Mar. 4, 2008

(54) FEEDBACK CANCELLATION WITH LOW FREQUENCY INPUT

(75) Inventors: Jakob Nielsen, Hellerup (DK); Michael Ekelid, Hellerup (DK)

(73) Assignee: Oticon A/S, Smørum (DK)

( * ) Notice: Subject to any disclaimer, the term of this patent is extended or adjusted under 35 U.S.C. 154(b) by 793 days.

(21) Appl. No.: 10/031,120

(22) PCT Filed: Jul. 7, 2000

(86) PCT No.: PCT/DK00/00380

§ 371 (c)(1),
(2), (4) Date: Apr. 23, 2002

(87) PCT Pub. No.: WO01/06812

PCT Pub. Date: Jan. 25, 2001

(30) Foreign Application Priority Data

Jul. 19, 1999 (DK) .............................. 1999 01043

(51) Int. Cl.
*A61F 11/06* (2006.01)
*G10K 11/16* (2006.01)
*H03B 29/00* (2006.01)

(52) U.S. Cl. ................................ 381/71.11; 381/71.12

(58) Field of Classification Search ................ 381/318, 381/71.11, 83, 93, 71.12, 71.8, 94.1, 94.9, 381/71.1

See application file for complete search history.

(56) References Cited

U.S. PATENT DOCUMENTS 4,175,258 A * 11/1979 Borkowski et al. ........... 331/78
4,658,426 A 4/1987 Chabries et al.
5,016,280 A 5/1991 Engebretson et al.
5,259,033 A 11/1993 Goodings et al.
5,444,786 A * 8/1995 Raviv ...................... 381/71.14
5,473,702 A * 12/1995 Yoshida et al. ............ 381/94.7
5,475,759 A * 12/1995 Engebretson ............... 381/318
5,661,814 A * 8/1997 Kalin et al. ................. 381/314
5,680,467 A * 10/1997 Hansen ....................... 381/314
5,748,751 A 5/1998 Janse et al.
5,835,607 A 11/1998 Martin et al.
6,389,440 B1 * 5/2002 Lewis et al. ................ 708/322
6,418,228 B1 * 7/2002 Terai et al. ................ 381/71.8
6,434,247 B1 * 8/2002 Kates et al. ................ 381/312
6,876,751 B1 * 4/2005 Gao et al. ................... 381/318

FOREIGN PATENT DOCUMENTS

DE EP 0579152 A1 * 1/1994
EP 0579152 1/1994

* cited by examiner

*Primary Examiner*—Vivian Chin
*Assistant Examiner*—Jason Kurr
(74) *Attorney, Agent, or Firm*—Dykema Gossett PLLC

(57) ABSTRACT

The invention relates to a method for canceling feedback in an acoustic system comprising a microphone, a signal path, a speaker and means for detecting presence of feedback between the speaker and the microphone, the method comprising providing a LMS algorithm for processing the signal; where the LMS algorithm operates with a predetermined adaptation speed when feedback is not present; where the LMS algorithm operates an adaptation speed faster than the predetermined adaptation speed when feedback is present, and where the means for detecting the presence of feedback is used to control the adaptation speed selection of the LMS algorithm. The invention further relates to a method comprising using a highpass filter to prevent low-frequency signals from entering the LMS algorithm. The invention still further relates to a method comprising using bandwidth detection means for determining the presence of a feedback signal. The invention also relates to hearing aids for implementing these methods.

10 Claims, 3 Drawing Sheets

FEEDBACK CANCELLATION WITH LOW FREQUENCY INPUT

TECHNICAL FIELD

The present invention concerns hearing aids. In many hearing aids, for example "In-the-ear" (ITE) and "Behind-the-ear" (BTE), the micro-phone and the receiver (telephone) components are placed close to each other. This may result in leaking of the sound produced by the receiver back into the microphone. This may occur when the hearing aid shell or the ear mould does not fit sufficiently tight in the ear canal. Given enough amplification in the hearing aid, the loop gain of the system may exceed 0 dB at some frequency and a feedback oscillation may be produced.

BACKGROUND OF THE INVENTION

The present invention is based on algorithms previously proposed in the literature. The invention concerns a number of algorithm modifications, which overcome some of the limitations of other systems used for feedback reduction in hearing aids.

The invention relates to a feedback cancellation algorithm which does not need an artificial noise signal in order to estimate the feedback transfer function. The input signal received from the environment, or the feedback oscillation signal, is used to drive the estimation process. In this fashion, the hearing aid user does not listen to an added noise signal, and a higher sound quality is possible. However, it is well known that such 'no-noise' algorithms can have audible side effects under certain circumstances, especially when environmental signals with long autocorrelation functions are present at the microphone.

The autocorrelation function for a signal describes the average correlation between two signal values, which are separated by a time difference "Lag". In loose terms, the autocorrelation function describes how "predictable" a signal value is, given the other samples in the signal. Some signals, for example periodic signals, are highly predictable and, correspondingly, the autocorrelation function does not vanish even for large values of Lag. Other signals, such as white noise, are very little predictable, and their autocorrelation function quickly vanish for increasing values of Lag. For signals with a long autocorrelation function, a future sample value can be predicted with a high degree of confidence, given the past samples. In other words, new samples of the signal do not provide much new information. Careful analysis of feedback cancellation systems reveal that signals with long autocorrelation may drive the adaptive system to produce poor estimates of the feedback path.

It is an objective of the present invention to provide a method and a hearing aid having means for feedback cancellation which improves the result of the feedback canceling by being more stable and thereby gives an improved user comfort.

SUMMARY OF THE INVENTION

According to the invention the first objective is achieved by a method for canceling feedback in an acoustic system that includes a microphone, a signal path, a speaker, means for detecting presence of feedback between the speaker and the microphone, and filter means for compensating at least partly a possible feedback signal, which includes using a LMS algorithm for generating filter coefficients; using a highpass filter to prevent low-frequency signals from entering the LMS algorithm; and using an additional feedback cancellation filter and a noise generator is used for providing low-frequency input for the LMS algorithm. According to the invention, the first objective is likewise achieved by a hearing aid which includes a microphone; a signal path; a amplifier; a speaker; means for detecting feedback between the speaker and the microphone; filter means for at least partly compensating a possible feedback signal; memory means including a LMS algorithm for generating filter coefficients; at least one highpass filter for preventing low-frequency signals from entering the LMS algorithm; and an additional feedback cancellation filter and a noise generator for providing low-frequency input for the LMS algorithm.

Hereby a more stable system is achieved. The stability is connected with the fact that the LMS algorithm is controlled in a more reliable manner, thereby providing more reliable coefficients to the feedback cancellation filter. This results in an improved user comfort.

The result of the method and the device is a more reliable feedback detection and hence an improved user comfort.

The present invention includes features, which can eliminate side effects in most cases and improve the adaptation speed resulting in fast suppression of feedback oscillations.

DETAILED DESCRIPTION OF THE DRAWINGS

Figure 1:
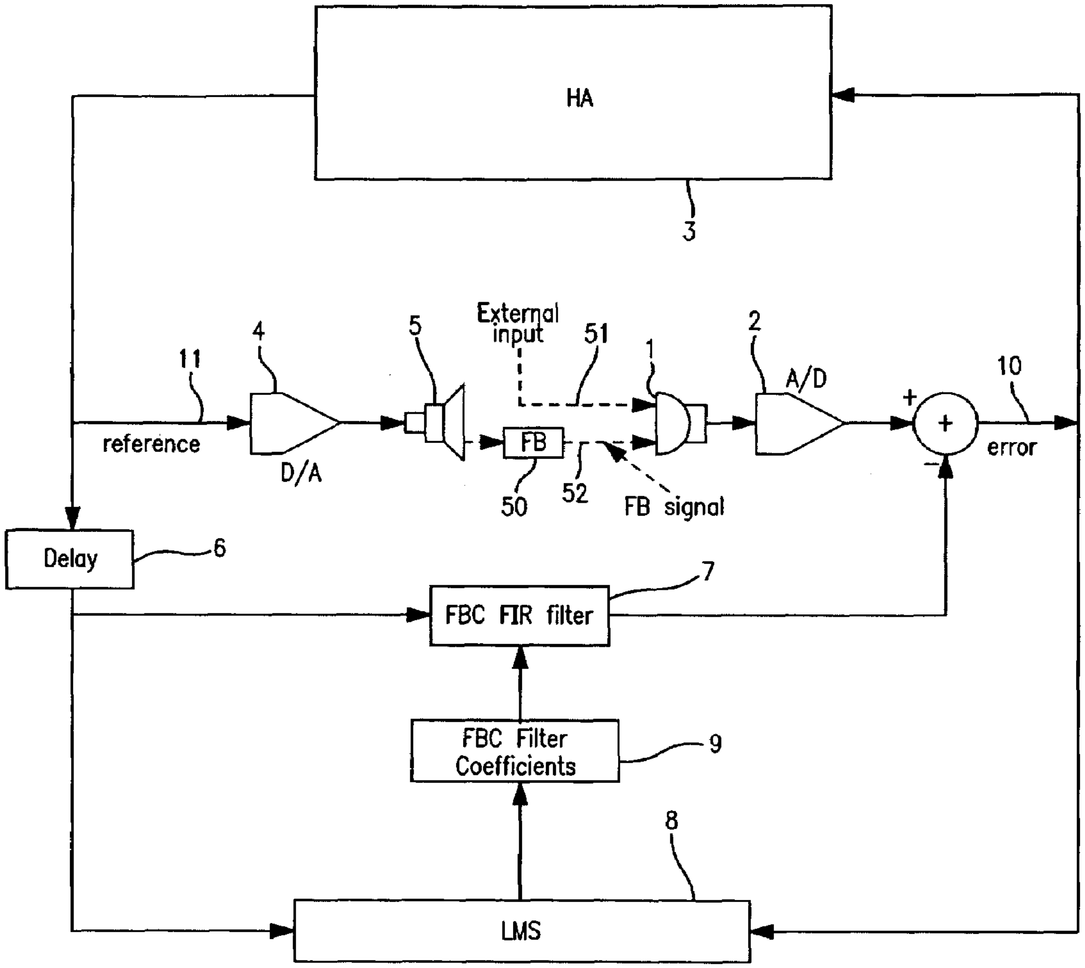
FIG. 1 (PRIOR ART)
FIG. 1 is a schematic diagram showing a previously known system used for feedback cancellation.

A well-known principle for feedback cancellation in hearing aids is shown in FIG. 1. All the components described below, except blocks (1), (5) and (50), operate in the discrete time domain.

The components are as follows: (1) is a microphone which picks up the sound from the environment (51) ("External input") and the feedback signal (52) ("FBSignal"); (2) is a microphone amplifier and an analog-to-digital converter (A/D); (3) is the hearing aid amplifier with filters, compressors, etc.; (4) is a digital-to-analog converter and a power amplifier; (5) is the hearing aid receiver; (50) is the acoustic feedback path (outside the hearing aid); (6) is a delay unit whose delay matches the delay through the components (4), (5), (50), (1) and (2). (7) is an N-tap finite impulse response (FIR) filter which is intended to simulate the combined impulse response of components (4), (5), (1), (2) and (50). (8) is an adaptive algorithm which will adjust the coefficients (9) of the filter (7) so as to minimize the power of the error signal (10).

The algorithm (8) is well known as the Least Mean Square (LMS) algorithm. The algorithm requires a reference signal (11), which is used to excite the path consisting of the components (4), (5), (1), (2) and (50). The correlation between the reference signal (11) and the error signal (10) is used to compute the adjustment of the coefficients (9).

The system utilizes the output signal (11) from the hearing aid amplifier block (3) as a driving signal for the LMS algorithm, thereby eliminating the need for a disturbing noise in the receiver (5).

For some external input signals, the LMS based algorithm used in the application shown in FIG. 1 is known to have difficulty adjusting the coefficients (9) as desired, i.e. to match the path consisting of components (4), (5), (1), (2) and (50). The difficulties are greatest for signals with long autocorrelation functions. Mismatched coefficients may lead to audible side effects, which can be very disturbing to a hearing aid user. Those may comprise audible oscillations and change in gain characteristics and frequency characteristics. One general remedy against this problem is to use a low adaptation speed, but this leads to poorer performance of the system because the coefficients cannot track changes in the acoustic feedback path (50) quickly, resulting in a long feedback cancellation time.

The basic system shown FIG. 1 may be improved in various ways to minimize the side effects associated with certain input signals. Many authors have proposed additional system blocks which will improve the sound quality while maintaining an acceptable adaptation speed.

The present invention is based on the system diagram shown in FIG. 1, and the invention consists of additional features which will improve the sound quality and maintain an acceptable adaptation speed.

The present invention is based on the system diagram shown in FIG. 1, and the invention consists of additional features, which will improve the sound quality and maintain an acceptable adaptation speed.

Figure 2:
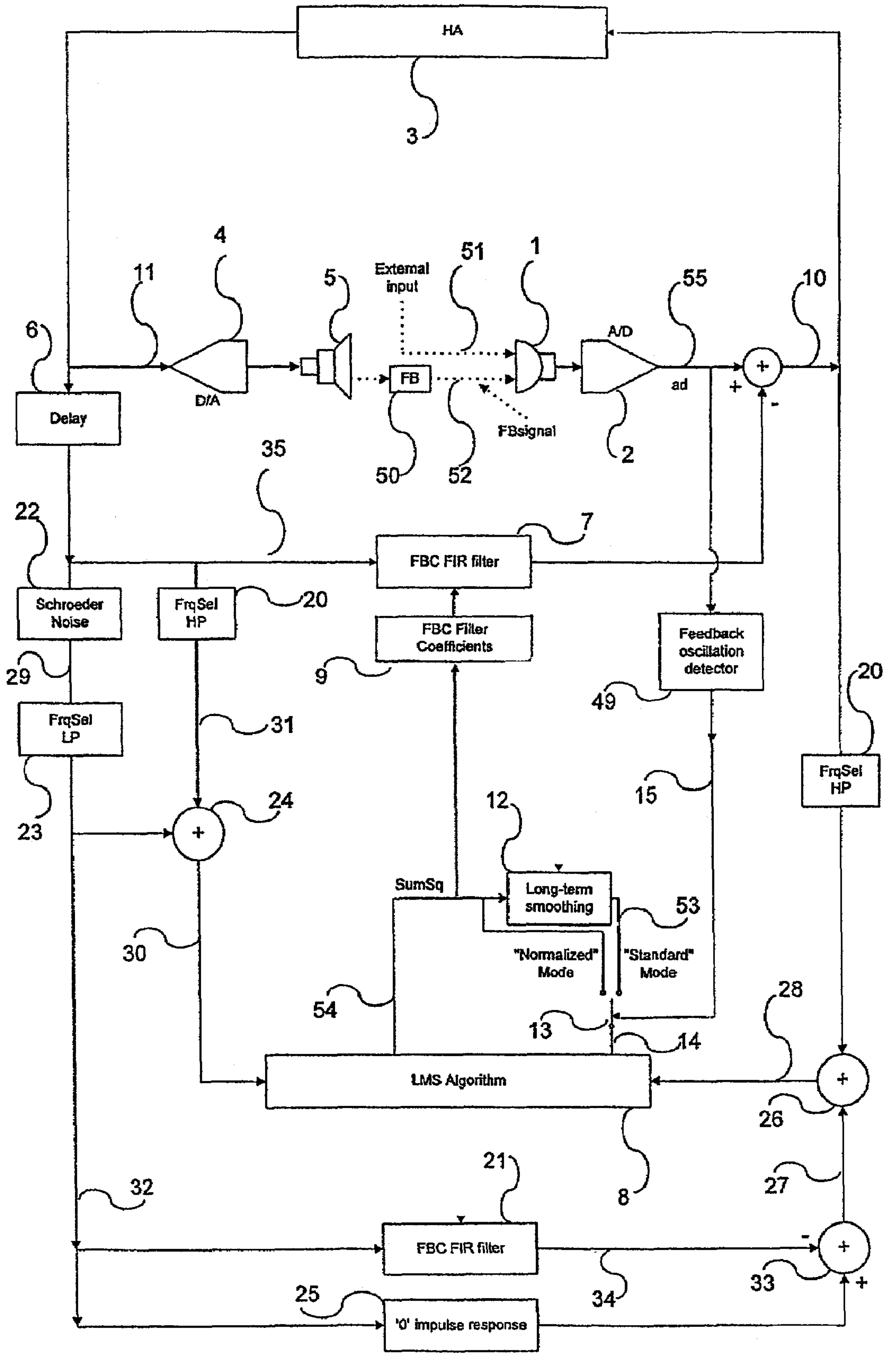
FIG. 2 is a schematic diagram showing an embodiment of the system according to the present invention.

FIG. 2 shows the block diagram of the general system and the components of the invention.

The embodiment shown includes three features: Adaptation rate control, a frequency-selective adaptation procedure, and a feedback oscillation detector.

Adaptation Rate Control

Two well known operation modes for the LMS algorithm are the "standard" mode and the "normalized" mode. In the "standard" mode, the coefficients are updated by an amount that depends on the short-term power of the error signal and the reference signal. This means that the update rate is faster when more powerful signals are processed by the hearing aid. In the "normalized" mode, the update rate is made nearly independent of the signal power, due to a normalization of the update equation.

As described earlier, a low adaptation speed generally improves the sound quality for signals with long autocorrelation functions. In contrast, a high adaptation speed is desirable to reduce feedback oscillations quickly.

Other authors have previously proposed changing the adaptation rate factor (often known as "μ") when feedback oscillations are detected. Although this does increase the adaptation speed, it also allows coefficients to deteriorate proportionally faster, in those situations where signals with long autocorrelation functions are present at the hearing aid input.

In the present invention, the fact that feedback oscillations often have a high power is used. In many hearing aids, the output level is limited by compressor circuits, and in many cases the maximum output level is well above the normally used output level, for example when speech and other environmental signal are present. It is therefore assume that the feedback oscillations have a higher power than the environmental signal, in most cases where feedback problems exist.

Additionally, the feedback oscillation has the desirable property that its frequency is generally equal to the frequency where the loop gain currently is highest, i.e. where the fastest adaptation is needed.

For the reasons mentioned above, it is very effective to utilize the feedback oscillation signal itself as a driving signal for the adaptation.

When the "normalized" adaptation approach is used, the high-power feature of the feedback oscillation is not utilized. If, instead, the "standard" update approach were used, the high power feature of the feedback oscillation would be utilized. At the same time, however, stronger signals in general would cause a higher adaptation speed, which could lead to more autocorrelation problems.

The present invention introduces a new normalization scheme, which will generally maintain the low adaptation speed and the normalized operation mode, except when a feedback oscillation is detected. When a feedback oscillation is detected, the system is switched from normalized operation to standard operation by the switch (13), and the full power of the feedback oscillation signal is therefore allowed to adapt the coefficients. During "standard" operation, the update parameter (14) is chosen to such a value (53) that the external input (51) produces approximately the same update rate as it would in "normalized" operation. Assuming that the external input signal (51) maintains nearly constant properties before and during the feedback oscillation, the switch of normalization procedure will be nearly transparent to the external signal (51). This ensures that the sound quality remains high, even though the adaptation speed has been increased due to the higher power in the feedback oscillation. The update parameter (53) to be used during standard mode is estimated in component (12) before the feedback oscillation is detected. During intervals of feedback oscillations, controls signal (15) prevents (12) from updating the parameter (53).

The switch from normalized mode to standard mode may be controlled by a feedback oscillation detector (49) through its output signal (15). The switch (13) may also be controlled by other conditions, which could result in feedback oscillations, for example when the acoustic feedback is rapidly decreased.

The adaptive LMS algorithm (8) may be implemented as the following set of equations:

Normalized Operation:

$$h_k(n+1) = h_k(n) + \frac{a \cdot r(n-k) \cdot e(n)}{b + \sum\limits_{p} r(n)^2}, \; p = 1 \ldots N \quad k = 1 \ldots N \tag{E1}$$

Standard Operation:

$$h_k(n+1) = h_k(n) + \frac{a \cdot r(n-k) \cdot e(n)}{b + LT_{sum}}, \; k = 1 \ldots N \tag{E2}$$

In these equations, $h_k(n)$ is the k'th coefficient in the FIR filter at sample time n; a is a constant which determines the general adaptation speed of the algorithm (this constant is sometimes referred to as "μ"); b is a small constant which prevents division by 0 for very small values of the reference signal; N is the number of coefficients in the filter (7); r(n) is the reference signal (30) sample value at time n; e(n) is the error signal (28) sample value at time n; and $LT_{Sum}$ is a value computed as described below.

The sum term of the denominator of E1 is equal to the signal (54). $LT_{sum}$ is equal to the signal (53).

$LT_{sum}$ (equal to (53)), which is computed by component (12), may be updated according to eq. (E3a):

$$LT_{sum}(n+1)=LT_{sum}(n)\cdot\beta_{LT}+\mathrm{Sum}Sq(n)\cdot\alpha_{LT} \quad (E3a)$$

In equation (E3a) SumSq(n) is defined as follows (E3b):

$$SumSq(n)=\sum^{p} r(n)^2,\ p=1\ \ldots\ N \quad (E3b)$$

$\alpha_{LT}$ and $\beta_{LT}$ are time constants, which control the length of the exponential window over which the value of $LT_{sum}$ is computed.

Eq. (E3a) should not be updated while a feedback oscillation is present, since $LT_{sum}$ should reflect the long-term value of SumSq for segments without oscillation. Once the feedback oscillation has disappeared, eq. (E3a) may be updated again.

In E1 and E3b, the reference signal r(n) is used for normalizing the update equation. However, other signals in the system shown in FIG. 2 may also be used instead of r(n). In the literature, the error signal e(n) has been used instead of r(n) for normalization; and even combinations of r(n) and e(n) have been used. The present invention will work for any type of normalization, in which the denominator in E1 and E2 is increased when the power level in the feedback loop consisting of (1), (2), (3), (4), (5) and (50) is increased.

Frequency-Selective Adaptation

Many feedback cancellation systems proposed earlier contain some form of frequency weighting of the signals which enter the LMS algorithm (8). The purpose of such weighting is to attenuate frequency ranges in which the autocorrelation of the external input signal (51) is long, and thereby reduce the possibility of poorly adjusted coefficients and poor sound quality. Several possibilities exist for frequency weighting. Various combinations of fixed and adaptive filters have been suggested in the past.

In the present invention, steep highpass filters with high attenuation (20) are included in the inputs to the LMS algorithm. The purpose of these filters is to prevent low frequency contents from the reference signal (11) from entering the LMS algorithm. The cutoff frequency for the highpass filters (20) must be lower than the lowest frequency for which feedback cancellation should take place, and otherwise as high as possible.

With the highpass filters (20) in place, the LMS algorithm (8) would not experience an increased level of the error signal (10) when the coefficients (9) are poorly adjusted in the low frequency range. Filter (7) with poorly adjusted coefficients, combined with components (3) and (6), may lead to a system with a high loop gain, and instabilities may result.

In order to avoid this problem, a parallel feedback cancellation filter (21) is added. This filter is intended to provide low frequency information to the LMS algorithm. The two filters (7) and (21) use identical coefficients (9). While filter (7) is designed to simulate the path consisting of components (4), (5), (1), (2) and (50), filter (21) is designed to simulate the artificial path (25) with an impulse response of constant '0'. The adder (33) computes an error signal as the difference between the desired '0' output and the actual output (34) from the filter (21). The error output (10) from the high frequency range and the error output (27) from the low frequency range are combined into a single error signal (28) which is fed to the error input of the LMS algorithm (8). In order to generate a low frequency signal as input to the filter (21) and to the reference input to the LMS algorithm, a noise generator (22) is included. The noise generator output (29) is lowpass filtered by a fixed filter (23). The cutoff frequency for the lowpass filter (23) is selected approximately equal to the cutoff frequency of the highpass filters (20), to obtain a reasonably flat input spectrum to the LMS algorithm. The low frequency signal (32) and the high frequency signal (31) are combined by the adder (24) to form the complete reference signal (30) for the LMS algorithm. Clearly, the components (25) and (33) may be removed immediately, and the signal (34) can be connected to the signal (27).

The noise generator (22) may be implemented by randomly swapping the numerical sign of each sample of the signal (35). In other words, for each sample instant it is randomly decided whether the sample value should be multiplied by 1 or by (−1). The advantage of using this type of noise generator is that noise samples at (35) and at (29) always have the same amplitude. The power spectrum of the reference signal (30) is therefore reasonably balanced at all times. In the literature, the noise generated as described above is sometimes referred to as 'Schroeder' noise.

Feedback Oscillation Detector

Feedback oscillations may be produced by a system which contains an amplifier and a feedback loop, under some circumstances. A hearing aid with acoustic amplification, combined with an acoustic path from the hearing aid telephone through a ventilation channel ("vent") and possibly other leaks, form a loop which may have a gain higher than 0 dB, at least for some frequencies. With more than 0 dB loop gain, the system may become unstable and produce feedback oscillations.

The present invention is designed to detect a feedback oscillation in the input signal (55), and set a flag (15) which indicates 'oscillation' or 'no oscillation'.

Some assumptions about the feedback oscillations in hearing aids are included in the design of the detector. The signal produced as a feedback oscillation typically consists of a single frequency, namely the frequency at which the loop gain is highest, taking into account both the linear and non-linear components of the hearing aid. The level of the feedback oscillation is relatively stable, after a certain settling time. The feedback oscillation often dominates the signal in the feedback loop, since its level is often determined by the hearing aid compressors.

The feedback detection process is complicated by the presence of other signals in the feedback loop. Many environmental signals, including music, may contain segments of periodic nature which may resemble a feedback oscillation. However, in the frequency range where oscillations may occur, relatively few environmental signals consist of a single frequency only, at least when considered over a period of a few hundred milliseconds or more.

The feedback oscillation detector in the present invention is based on measuring the overall 'bandwidth' of the signal in the feedback loop consisting of components (1), (2), (3), (4), (5) and (50). In the preferred embodiment, the signal (55) is used as input to the detector, but with slight modifications the detector may obtain its input anywhere in the loop. When the bandwidth of the signal (55) has been small for a certain minimum period of time, the detector will flag a 'feedback oscillation' condition.

Figure 3:
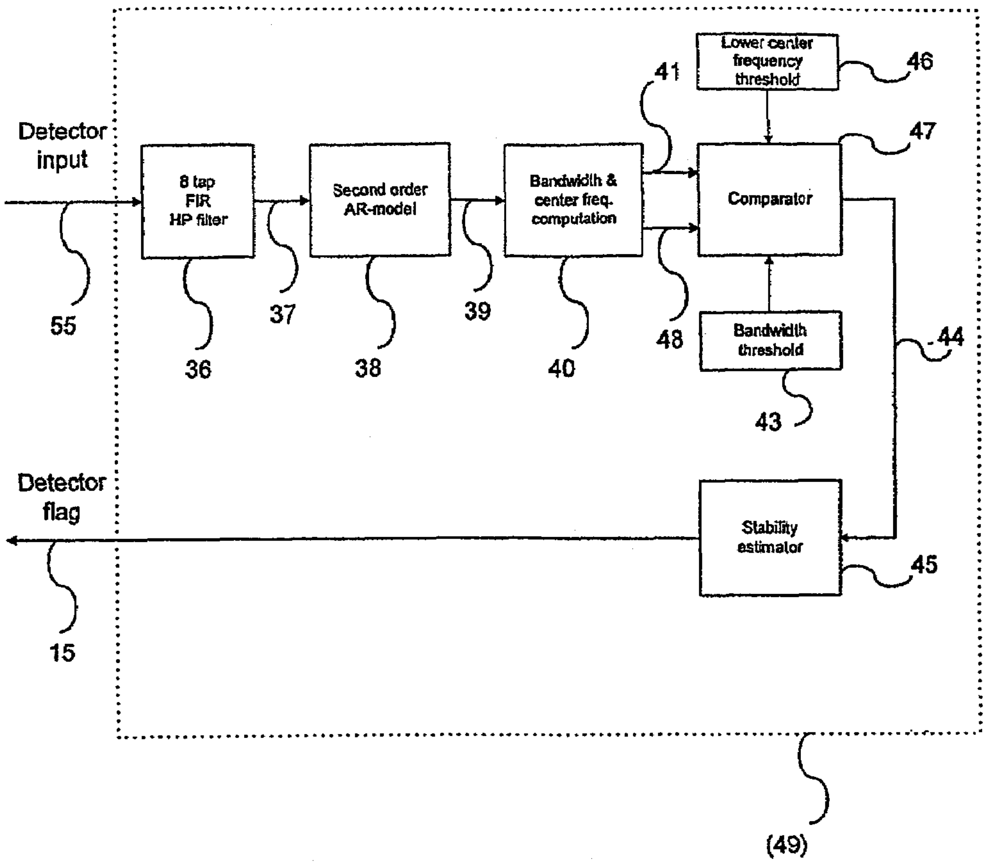
FIG. 3 is a schematic diagram showing the feedback detection system according to the invention.

FIG. 3 describes the detector (49). The input signal (55) is highpass filtered by an 8-tap FIR filter (36). The filter helps prevent false feedback oscillation detection for low frequency input signals since it suppresses the fundamental frequencies for a wide range of signals. The 3 dB roll-off frequency for the filter should be higher than the lowest expected feedback oscillation frequency. The 8-tap FIR filter is just one example of a usable filter, but many other types may be used. The highpass filtered signal (37) is fed to a modeling device (38), which attempts to model the spectrum of the signal (37), using a second-order auto-regressive model as shown in E4:

$$y(n)=x(n)\cdot K-a_1y(n-1)-a_2y(n-2) \quad \text{(E4)}$$

where x(n) represents the excitation signal, which drives the model input, while y(n) is the output from the model.

The signal model E4 represents a second-order IIR filter with a single complex-conjugated pole-pair. Based on the model coefficients $a_1$ and $a_2$ (39), the filters center frequency and bandwidth may be computed. This computation is performed by the unit (40), which produces a bandwidth (41) and a center frequency (48). These two values are compared by (47) to preset thresholds (43) and (46). The comparator sets flag (44) TRUE if the bandwidth (41) is lower than the preset threshold (43) AND the center frequency (48) is higher than the acceptable minimum feedback oscillation frequency (46). Otherwise the flag (44) is set FALSE.

All components (38), (40), (47) and (45) are working on a frame based schedule. A frame length of 40 ms may be used, but other values of the length would also work. For each frame, a new value of the flag (44) is computed. Since many environmental input signals contain short segments of narrow bandwidth, the flag (44) may occasionally be set TRUE while no feedback oscillations are present. To avoid this, the flag (44) is fed to a stability estimator (45). In here, the flag (44) is placed in a delay line which, at any point in time, holds the values of the flag from the last $N_{se}$ frames. $N_{se}$ may be selected as 10, but other values would also work. The stability estimator (45) sets the detector flag (15) TRUE when and only when at least $N_{min}$ out of the $N_{se}$ past values of the flag (44) were TRUE. For example, $N_{min}$ may be set to 4.

The coefficients $a_1$ and $a_2$ in E4 are computed from the autocorrelation coefficients R(0), R(1) and R(2), by solving the equations:

$$R(0)\cdot a_1+R(1)\cdot a_2=-R(1) \quad \text{(E5a)}$$

$$R(1)\cdot a_1+R(0)\cdot a_2=-R(2) \quad \text{(E5b)}$$

The autocorrelation coefficients may be computed using the following equations:

$$R(0)=\frac{1}{N_f}\cdot\sum x(n)^2,\ n=1\ \ldots\ N_f \quad \text{(E6a)}$$

$$R(1)=\frac{1}{N_f}\cdot\sum x(n)\cdot x(n+1),\ n=1\ \ldots\ N_f-1 \quad \text{(E6b)}$$

$$R(2)=\frac{1}{N_f}\cdot\sum x(n)\cdot x(n+2),\ n=1\ \ldots\ N_f-2 \quad \text{(E6c)}$$

where $N_f$ corresponds to the frame length, and x(i) is the i'th sample of signal (37) from the current frame.

The 3-dB bandwidth of the filter represented by the auto-regressive model E4 may be computed as $$\text{Bandwith}=2\cdot(1-\sqrt{a_2}) \quad \text{(E7)}$$

and the center frequency may be computed as $$f_{Center}=\cos^{-1}\left(\frac{-a_1}{2\sqrt{a_2}}\right) \quad \text{(E8)}$$

In both equations (E7) and (E8) the result is given in radians. Simple calculations, in which the system sample rate is included, may be used to convert the values of Bandwidth and the $f_{Center}$ into Hz.

In the previous description the hearing aid and the methods have been described in a simplified manner. Necessary elements like a power source, e.g. a battery, and related wiring, the signal processing capabilities of the hearing aid amplifier and the interconnecting wiring of the components, as well as the housing, which is always present have been omitted from the general definition of the hearing aid according to the invention. It should be appreciated that these elements of course are present in a hearing aid actually manufactured.

The invention claimed is:

1. A method for canceling feedback in an acoustic system comprising a microphone, a speaker, a signal path between the microphone and the speaker, means for detecting presence of feedback between the speaker and the microphone, and first adaptive feedback cancellation filter means for compensating at least partly a possible feedback signal, the method comprising:

using a LMS algorithm for generating filter coefficients for the first adaptive feedback cancellation filter means and for generating identical filter coefficients for a second adaptive feedback cancellation filter means;

using at least one highpass filter to prevent low-frequency signals from the signal path from entering the LMS algorithm; and using the second adaptive feedback cancellation filter means and a noise generator for providing low-frequency input for the LMS algorithm.

2. A method according to claim 1, where a Schroeder noise generator is used for generating a broad band noise signal having an amplitude substantially equal to the amplitude of the signal from which it was derived.

3. A method according to claim 2, where a steep low pass filter is used to generate a low-frequency noise signal to be used as the low-frequency input to the LMS algorithm.

4. A method according to claim 3, wherein a cutoff frequency for the lowpass filter is selected approximately equal to a cutoff frequency of the highpass filter(s).

5. A method according to claim 1, where the LMS algorithm operates with a predetermined essentially level independent adaptation speed when feedback is not present, this representing a first mode;

where the LMS algorithm operates at a level dependent adaptation speed when feedback is present, this representing a second mode;

where the means for detecting the presence of feedback is used to control the adaptation mode selection of the LMS algorithm; and where the adaptation speed for the LMS algorithm is determined by a long-term average of a denominator in the LMS update algorithm in the second mode.

6. A method according to claim 5, whereby bandwidth detection means are used for determining the presence of a feedback signal.

7. A method according to claim 6, where the stability of the signal determined as a feedback signal is analyzed.

8. A method according to claim 7, where the feedback analyzing comprises holding flag values from a number of succeeding time frames and comparing of these.

9. A hearing aid comprising:

a microphone;

a speaker;

a signal path between the microphone and the speaker, and which includes an amplifier;

means for detecting feedback between the speaker and the microphone;

first adaptive feedback cancellation filter means for at least partly compensating a possible feedback signal;

memory means including a LMS algorithm for generating filter coefficients for the first adaptive feedback cancellation filter means and for generating identical filter coefficients for a second adaptive feedback cancellation filter means;

at least one highpass filter for preventing low-frequency signals from the signal path from entering the LMS algorithm; whereby the second adaptive feedback cancellation filter means and a noise generator provides low-frequency input for the LMS algorithm.

10. A hearing aid according to claim 9, further comprising steep low pass filters for generating a low-frequency noise signal to be used as the low-frequency input to the LMS algorithm.

* * * * *